United States Patent [19]

End et al.

[11] Patent Number: 5,453,447
[45] Date of Patent: Sep. 26, 1995

[54] PREPARATION OF STABLE INJECTABLE β-CAROTENE SOLUBILIZATES

[75] Inventors: Lutz End, Mannheim; Dieter Horn, Heidelberg; Erik Lueddecke, Mutterstadt; Jachim U. Schneider, Weisenheim; Peter P. Hoppe, Wachenheim; Friedrich-Wilhelm Rensmann, Bad Duerkheim, all of Germany

[73] Assignee: BASF Aktiengesellschaft, Ludwigshafen, Germany

[21] Appl. No.: 769,025

[22] Filed: Oct. 1, 1991

[30] Foreign Application Priority Data

Oct. 2, 1990 [DE] Germany ............................ 40 31 094.9

[51] Int. Cl.⁶ .................... A61K 31/015; A61K 37/22; B01J 13/02; C07C 403/24
[52] U.S. Cl. .................... 514/763; 264/4.1; 424/450; 585/351
[58] Field of Search ............................ 424/450; 514/763; 264/4.1; 585/351, 866

[56] References Cited

U.S. PATENT DOCUMENTS

| | | | |
|---|---|---|---|
| 2,976,024 | 3/1961 | Martinek | 259/4 |
| 3,932,634 | 1/1976 | Kardys | 424/237 |
| 4,075,333 | 2/1978 | Josse | 424/237 |
| 4,435,427 | 3/1984 | Hoppe et al. | 514/763 |

FOREIGN PATENT DOCUMENTS

| | | |
|---|---|---|
| 0055817 | 7/1982 | European Pat. Off. |
| 89/07929 | 9/1989 | WIPO |

Primary Examiner—Thurman K. Page
Assistant Examiner—Carlos Azpuru
Attorney, Agent, or Firm—Keil & Weinkauf

[57] ABSTRACT

A process for the continuous preparation of Beta-carotene together with an emulsifier by briefly heating Beta-carotene together with an emulsifier to give a homogeneous solution, rapidly cooling the latter to below 100° C. by adding water, and subsequently adjusting to the required final concentration of Beta-carotene, comprises pumping a suspension, which has been preheated from 20° to 80° C., of 1 to 40% by weight of Beta-carotene in an emulsifier through a heating coil located in a heat transfer oil, where the solubilization mixture is at from 120° to 180° C. and the residence time is from 10 to 300 seconds, and subjecting the homogenous solution to turbulent mixing in a mixing chamber with an amount of water at from 10° to 80° C. to result in a solubilizate which contains from 0.5 to 6% by weight of Beta-carotene and is, if necessary, diluted to the required final concentration.

9 Claims, 1 Drawing Sheet

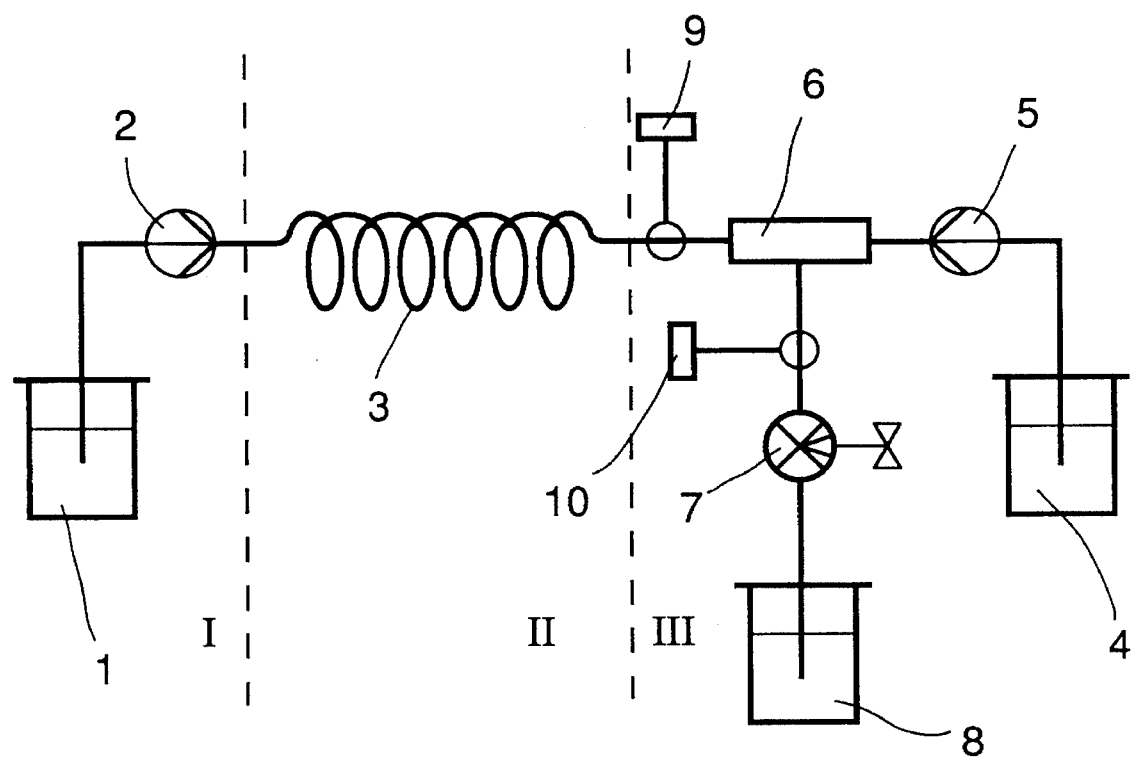

PREPARATION OF STABLE INJECTABLE β-CAROTENE SOLUBILIZATES

The present invention relates to the continuous preparation of β-carotene solubilizates by a mixing chamber process.

In a batch process described in EP-B-055 817 an aqueous β-carotene solution for injection is prepared using an emulsifier. For this, the emulsifier is heated to from 170° to 180° C., and β-carotene is introduced into the melt, when the β-carotene dissolves with partial isomerization. After a residence time of about 6 minutes, the melt is cooled to 95° C. and then water is introduced, initially dropwise, and the product is finally adjusted to an active substance content of 4.5% with water. The emulsifier content is usually about 25%.

Because of the low solubility of β-carotene, the solubilizate must demonstrate adequate stability in respect of recrystallization in a storage test, which is ensured by an optimal isomer ratio. Thus the preparation of a product which meets this specification must involve control of the isomerization. This can be achieved only with difficulty in the batch process described.

It is an object of the present invention to propose a continuous preparation process which involves control of the isomerization.

We have found that this object is achieved by a process for the continuous preparation of β-carotene solubilizates by briefly heating β-carotene together with an emulsifier to give a homogeneous solution, rapidly cooling the latter to below 100° C. by adding water, and subsequently adjusting to the required final concentration of β-carotene, which comprises pumping a suspension, which has been preheated to from 20° to 80° C., of from 1 to 40% by weight of β-carotene in an emulsifier through a heating coil located in a heat-transfer oil, where the solubilization mixture is at from 120° to 180° C. and the residence time is from 10 to 300 seconds, and subjecting the homogeneous solution to turbulent mixing in a mixing chamber, where appropriate under a pressure of from 10 to 50 bar, with an amount of water at from 10° to 80° C. to result in rapid cooling of the homogeneous solution to under 100° C. and in a solubilizate which contains from 0.5 to 5% by weight of β-carotene and is, if necessary, diluted to the required final concentration.

The mixing chamber can be in the shape of a T in which the water impinges on the β-carotene solution at an angle of about 180°. The crucial point about the shape of the mixing chamber is that it ensures turbulent mixing of the homogeneous solution and the aqueous phase.

Suitable emulsifiers are conventional non-ionic emulsifiers with an HLB (cf. H.P. Fiedler, Lexikon der Pharmazie, Kosmetik und angrenzenden Gebiete, 1971, pages 263–270, especially pages 267–269) of from 12 to 16, especially ethoxylated triglycerides of fatty acids with from 12 to 18 carbon atoms, which contain from 20 to 60 oxyethylene units, or ethoxylated sorbitan fatty acid esters with about 20 oxyethylene units or ethoxylated monohydroxy fatty acids with from 14 to 17 oxyethylene units, as are described in DE-A 29 11 241. Emulsifiers of this type are also called solubilizers because they dissolve in water and thus promote the dissolution of lipophilic substances by keeping them in micellar solution. Micellar solutions are distinguished by transparency and clarity. They can be characterized by stating the size of the micelles as determined by quasi-elastic light scattering. The diameters are from 10 to 100 nm, depending on the solubilizer used and the content of active substance.

Examples of particularly suitable non-ionic emulsifiers are:
Glycerol polyoxyethylene glycol ricinoleate, glycerol polyoxyethylene glycol hydroxystearate, polyoxyethylene(20) sorbitan monooleate, polyoxyethylene(20) sorbitan monostearate and monohydroxystearic acid with 15 oxyethylene units.

BRIEF DESCRIPTION OF THE DRAWING

The drawing depicts the apparatus used for this process.

The solubilizates are prepared by the novel process using, for example, an apparatus as depicted diagrammatically in FIG. 1, as follows:

The apparatus is divided into parts I, II and III. Part II is the high-temperature section while the temperatures in parts I and III are below 80° C.

A suspension of β-carotene in the selected emulsifier at a concentration of 1–40%, preferably 10–30% by weight, with or without the addition of 0.1–10% of antioxidants, is introduced into the vessel (1). The suspension is adjusted to from 20° to 80° C., preferably to 60°–70° C. The pump (2) continuously feeds the active substance suspension into the heating coil (3). The latter is located in a heated heat-transfer oil. The delivery of the pump (2), the length of the heating coil (3) and the temperature of the heat-transfer oil are mutually adjusted so that the residence time of the suspension in the heating coil is from 10 to 300 sec (preferably 60 sec) at a temperature of from 120° to 180° C. measured at the measurement point (9). During this residence time, the β-carotene dissolves in the solubilizer with simultaneous isomerization. The solution emerging from the heating coil is subjected to turbulent mixing in the mixing chamber (6) with the aqueous phase which is likewise conveyed by the pump (5) from the container (4) into the mixing chamber. A micellar β-carotene solution is produced in the mixing chamber. The aqueous phase is at from 10° to 80° C., preferably at 25° C. The aqueous phase can contain a preservative, for example benzyl alcohol, in a concentration of from 0.5 to 5% of the final product. The temperature of the solubilizate downstream of the mixing chamber is measured at the measurement point (10) and is from 40° to 80° C. The product is discharged through the pressure control (7) which is set at 10–50 bar into the container (8). The content of active substance depends on the concentrations and stream quantities chosen in each case and is usually from 0.5 to 5%, preferably 4%.

Examples of conventional antioxidants which can also be used in the novel process are: butylated hydroxytoluene or hydroxyanisole and d,1-α-tocopherol. The antioxidants are generally used in amounts of from 10 to 20% of the weight of β-carotene employed.

It is also expedient to use conventional approved preservatives such as β-phenylethyl alcohol, β-phenoxyethyl alcohol and benzyl alcohol, especially benzyl alcohol.

The novel process can be used to prepare β-carotene solubilizates which provide outstandingly stable solutions for injection. The bioavailability of the injectable β-carotene solubilizates is higher than that of orally administered β-carotene. The higher bioavailability is indicated by maximum β-carotene levels in the blood which, for example in horses, cattle and pigs, are 1–2 powers of 10 higher than after oral administration. Injection of β-carotene solubilizates can be used to improve the fertility of agricultural livestock such as horses, cattle, pigs and rabbits by increasing the percentage of pregnant animals and the number of live births.

Control of the thermal isomerization in the novel process can be achieved by the choice of the dissolving temperature and the residence time to result in an isomer ratio which is optimal for storage stability and biological activity.

EXAMPLE

A suspension of X g of β-carotene (cf. table) in 250 g of 13-hydroxystearic acid ethoxylate and 10 g of butylatedhydroxytoluene was placed in a preheated vessel at 70° C. The suspension was fed by a high-pressure pump (2) at a rate of 2 l/h into the heating coil immersed in an oil bath. For an internal diameter of 2 mm and a length of 3 m, 6 m or 12 m with the heat-transfer oil at about 160° C., the residence time was set at 17, 34 or 68 seconds respectively. These times were sufficient to dissolve the β-carotene in the emulsifier in all cases. After the said residence time in the heating coil, the β-carotene solution entered a T-shaped mixing chamber where it underwent turbulent mixing at 180° with 690 g of deionized water delivered at 5 l/h by the high-pressure pump (5). Under a pressure of 25 bar, the product was discharged through a pressure-control valve. The result in all cases was a dark red micellar β-carotene solution. The product was at 60° C. The active substance content was from 4.3 to 5.5% depending on the procedure. The micelle diameter in the solubilizates measured by quasi-elastic light scattering was 20–30 nm.

The table shows all the experimental parameters and measured data, including the isomer ratios found.

the latter to below 100° C. by adding water, which process comprises continuously feeding containing from 1 to 40% by weight of β-carotene in an emulsifier and which has been preheated to a temperature of from 20° to 80° C. by means of a pump through a heating coil located in a heat-transfer oil, where the solubilization mixture is at from 120° to 180° C. and the residence time is from 10 to 300 seconds, and subjecting the homogeneous solution to turbulent mixing in a mixing chamber with an amount of water at from 10° to 80° C. to result in a solubilizate which contains from 0.5 to 6% by weight of β-carotene.

2. A process as defined in claim 1, wherein the mixing chamber has approximately the shape of a T in which the water impinges on the hot β-carotene solution at an angle of about 180°.

3. A process as claimed in claim 1, wherein a nonionic emulsifier with an HLB of from 12 to 16, is used.

4. A process as defined in claim 3, wherein the nonionic emulsifier used is ethoxylated monohydroxystearic acid with 15 oxyethylene units.

5. A process as defined in claim 1, wherein the homogeneous solution is subjected to turbulent mixing with the water in the mixing chamber Under a pressure which has been raised to 10 to 50 bar.

6. A process as defined in claim 1, wherein an antioxidant is added to the suspension.

7. A process as defined in claim 1, wherein the antioxidant is butylated hydroxytoluene or butylated hydroxyanisole or d,1-α-tocopherol in an amount of from 10 to 20% of the weight of β-carotene.

8. A process as defined in claim 1, wherein a preservative is added to the suspension.

TABLE

| | | Heating coil | | | | Characterization of the solubilizate | | | | | |
|---|---|---|---|---|---|---|---|---|---|---|---|
| | β-Carotene | | Residence | Temperatures | | β-Carotene | Micelle | | Isomer content | | |
| Experiment no. | weight [g] | Length [m] | time [sec] | Solution [°C.] | Solubilizate [°C.] | content [% by wt.] | size [nm] | pH | all-trans [%*)] | 13-cis [%*)] | 9-cis [%*)] |
| 1 | 50 | 3 | 17 | 158 | 58 | 4.9 | 30 ± 25% | 7.0 | 66.4 | 18.1 | 4.1 |
| 2 | 50 | 12 | 68 | 153–160 | 57 | 4.5 | 21 ± 30 | 6.9 | 36.9 | 21.7 | 22.5 |
| 3 | 42.5 | 12 | 68 | 150 | 60 | 4.3 | 20 ± 22 | 7.0 | 38.0 | 20.7 | 21.9 |
| 4 | 42.5 | 3 | 17 | 159 | 60 | 4.5 | 20 ± 22 | 6.7 | 56.6 | 23.2 | 5.3 |
| 5 | 42.5 | 6 | 34 | 169 | 61 | 4.6 | 21 ± 20 | 7.0 | 50.6 | 17.5 | 16.4 |
| 6 | 50 | 6 | 34 | 162 | 64 | 5.5 | 22 ± 28 | 6.7 | as Experiment No. 5 | | |

*)area in HPLC at 450 nm

We claim:

1. A continuous process for the preparation of β-carotene solubilizates by briefly heating carotene together with an emulsifier to give a homogeneous solution, rapidly cooling 9. A process as defined in claim 8, wherein benzyl alcohol is used as preservative.

* * * * *

UNITED STATES PATENT AND TRADEMARK OFFICE
CERTIFICATE OF CORRECTION

PATENT NO.: 5,453,447

DATED: September 26, 1995

INVENTOR(S): END et al.

It is certified that error appears in the above-identified patent and that said Letters Patent is hereby corrected as shown below:

Column 3, claim 1, line 50, after "heating" insert -- β --

Column 4, cliam 1, line 2, after "feeding" insert --a β-carotene suspension--.

Signed and Sealed this

Sixth Day of February, 1996

BRUCE LEHMAN

*Attest:*

*Attesting Officer*   Commissioner of Patents and Trademarks